United States Patent
Abbas et al.

(10) Patent No.: US 8,815,571 B2
(45) Date of Patent: Aug. 26, 2014

(54) INCREASED FIBER HYDROLYSIS BY PROTEASE ADDITION

(75) Inventors: Charles A. Abbas, Champaign, IL (US); Wu-Li Bao, Champaign, IL (US)

(73) Assignee: Archer Daniels Midland Co., Decatur, IL (US)

( * ) Notice: Subject to any disclaimer, the term of this patent is extended or adjusted under 35 U.S.C. 154(b) by 1371 days.

(21) Appl. No.: 12/247,499

(22) Filed: Oct. 8, 2008

(65) Prior Publication Data

US 2009/0098638 A1    Apr. 16, 2009

Related U.S. Application Data

(60) Provisional application No. 60/998,818, filed on Oct. 12, 2007.

(51) Int. Cl.
| | | |
|---|---|---|
| *C13B 5/00* | (2011.01) | |
| *C12N 9/62* | (2006.01) | |
| *C12P 19/20* | (2006.01) | |
| *C12P 19/02* | (2006.01) | |
| *C12N 9/42* | (2006.01) | |
| *C12N 9/50* | (2006.01) | |
| *C12N 9/58* | (2006.01) | |
| *C12P 7/10* | (2006.01) | |

(52) U.S. Cl.
CPC  *C12P 19/02* (2013.01); *C12P 19/20* (2013.01)
USPC ........... 435/276; 435/277; 435/209; 435/219; 435/223; 435/225

(58) Field of Classification Search
CPC ............. A23K 1/06; C12P 7/10; C12P 19/02; C12P 19/20; C08L 97/02
See application file for complete search history.

(56) References Cited

U.S. PATENT DOCUMENTS

| | | | |
|---|---|---|---|
| 4,737,365 A | 4/1988 | Meyer | |
| 5,612,055 A | 3/1997 | Bedford et al. | |
| 6,506,423 B2 | 1/2003 | Drouillard et al. | |
| 7,005,128 B1 | 2/2006 | Bedford et al. | |
| 7,494,675 B2 * | 2/2009 | Abbas et al. ................. | 426/12 |
| 2004/0053373 A1 | 3/2004 | Foody et al. | |
| 2004/0202697 A1 | 10/2004 | Beauchemin et al. | |
| 2006/0154353 A1 | 7/2006 | Duan et al. | |
| 2006/0200877 A1 | 9/2006 | Lanahan et al. | |
| 2006/0251764 A1 * | 11/2006 | Abbas et al. ................. | 426/53 |
| 2007/0037259 A1 | 2/2007 | Hennessey et al. | |
| 2007/0124833 A1 | 5/2007 | Abad et al. | |

FOREIGN PATENT DOCUMENTS

JP    07031393 A  *  2/1995

OTHER PUBLICATIONS

Nebraska Ethanol Board "Ethanol Facts: Distillers Grains (DDG) and Corn Gluten Feed.", Apr. 3, 2005, retrieved online from <URL:http://www.ne-ethanol.org/facts/ddg.htm>, 1 page.*
International Preliminary Report on Patentability for PCT/US08/79152 (Form PCT/IB/373 and PCT/ISA/237), 7 pages.

* cited by examiner

*Primary Examiner* — Jon P Weber
*Assistant Examiner* — Aaron J Kosar

(57) ABSTRACT

Novel fiber processing methods and the products obtained therefrom are disclosed. Methods may include thermochemical and/or enzymatic hydrolysis of fiber feedstocks including distillers' dried grains, distillers' dried grains with solubles, soyhull, miscanthus and switchgrass. Enzymatic hydrolysis includes hydrolysis with cellulase, hemicellulase, and protease.

19 Claims, No Drawings

SEQUENCE LISTING

<160> NUMBER OF SEQ ID NOS: 12

<210> SEQ ID NO 1
<211> LENGTH: 394
<212> TYPE: PRT
<213> ORGANISM: Aspergillus saitoi

<400> SEQUENCE: 1

```
Met Val Val Phe Ser Lys Thr Ala Ala Leu Val Leu Gly Leu Ser Thr
1               5                   10                  15

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Val Asn Leu Pro Gly
        35                  40                  45

Leu Tyr Ala Arg Ser Leu Ala Lys Phe Gly Gly Thr Val Pro Gln Ser
    50                  55                  60

Val Lys Glu Ala Ala Ser Lys Gly Ser Ala Val Thr Thr Pro Gln Asn
65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Val Phe Ser Asp
            100                 105                 110

Glu Leu Pro Ser Ser Glu Gln Thr Gly His Asp Leu Tyr Thr Pro Ser
        115                 120                 125

Ser Ser Ala Thr Lys Leu Ser Gly Tyr Ser Trp Asp Ile Ser Tyr Gly
    130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ala Ser Lys Ile
                165                 170                 175

Ser Ser Glu Phe Val Gln Asp Thr Ala Asn Asp Gly Leu Leu Gly Leu
            180                 185                 190

Ala Phe Ser Ser Ile Asn Thr Val Gln Pro Lys Ala Gln Thr Thr Phe
        195                 200                 205

Phe Asp Thr Val Lys Ser Gln Leu Asp Ser Pro Leu Phe Ala Val Gln
    210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
                245                 250                 255
```

```
Gly Tyr Trp Gly Phe Ser Thr Asp Gly Tyr Ser Ile Gly Asp Gly Ser
                260                 265                 270

Ser Ser Ser Ser Gly Phe Ser Ala Ile Ala Asp Thr Gly Thr Thr Leu
            275                 280                 285

Ile Leu Leu Asp Asp Glu Ile Val Ser Ala Tyr Tyr Glu Gln Val Ser
        290                 295                 300

Gly Ala Gln Glu Ser Tyr Glu Ala Gly Gly Tyr Val Phe Ser Cys Ser
305                 310                 315                 320

Thr Asp Leu Pro Asp Phe Thr Val Val Ile Gly Asp Tyr Lys Ala Val
                325                 330                 335

Val Pro Gly Lys Tyr Ile Asn Tyr Ala Pro Val Ser Thr Gly Ser Ser
            340                 345                 350

Thr Cys Tyr Gly Gly Ile Gln Ser Asn Ser Gly Leu Gly Leu Ser Ile
        355                 360                 365

Leu Gly Asp Val Phe Leu Lys Ser Gln Tyr Val Val Phe Asn Ser Glu
    370                 375                 380

Gly Pro Lys Leu Gly Phe Ala Ala Gln Ala
385                 390

<210> SEQ ID NO 2
<211> LENGTH: 394
<212> TYPE: PRT
<213> ORGANISM: Aspergillus niger

<400> SEQUENCE: 2

Met Val Val Phe Ser Lys Thr Ala Ala Leu Val Leu Gly Leu Ser Thr
1               5                   10                  15

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Val Asn Leu Pro Gly
        35                  40                  45

Leu Tyr Ala Arg Ser Leu Ala Lys Phe Gly Gly Thr Val Pro Gln Ser
    50                  55                  60

Val Lys Glu Ala Ala Ser Lys Gly Ser Ala Val Thr Thr Pro Gln Asn
65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Gly Phe Ser Asp
            100                 105                 110

Glu Leu Pro Ser Ser Glu Gln Thr Gly His Asp Leu Tyr Thr Pro Ser
        115                 120                 125

Ser Ser Ala Thr Lys Leu Ser Gly Tyr Ser Trp Asp Ile Ser Tyr Gly
    130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ser Lys Ile
                165                 170                 175

Ser Ser Glu Phe Val Gln Asp Thr Ala Asn Asp Gly Leu Leu Gly Leu
            180                 185                 190

Ala Phe Ser Ser Ile Asn Thr Val Gln Pro Lys Ala Gln Thr Thr Phe
        195                 200                 205

Phe Asp Thr Val Lys Ser Gln Leu Asp Ser Pro Leu Phe Ala Val Gln
    210                 215                 220

Leu Lys His Asp Ala Pro Gly Val Tyr Asp Phe Gly Tyr Ile Asp Asp
```

```
            225                 230                 235                 240
Ser Lys Tyr Thr Gly Ser Ile Thr Tyr Thr Asp Ala Asp Ser Ser Gln
                245                 250                 255

Gly Tyr Trp Gly Phe Ser Thr Asp Gly Tyr Ser Ile Gly Asp Gly Ser
            260                 265                 270

Ser Ser Ser Ser Gly Phe Ser Ala Ile Ala Asp Thr Gly Thr Thr Leu
        275                 280                 285

Ile Leu Leu Asp Asp Glu Ile Val Ser Ala His Tyr Glu Gln Val Ser
    290                 295                 300

Gly Ala Gln Glu Ser Tyr Glu Ala Gly Gly Tyr Val Phe Ser Cys Ser
305                 310                 315                 320

Thr Asp Leu Pro Asp Phe Thr Val Val Ile Gly Asp Tyr Lys Ala Val
                325                 330                 335

Val Pro Gly Lys Tyr Ile Asn Tyr Ala Pro Val Ser Thr Gly Ser Ser
            340                 345                 350

Thr Cys Tyr Gly Gly Ile Gln Ser Asn Ser Gly Leu Gly Leu Ser Ile
        355                 360                 365

Leu Gly Asp Val Phe Leu Lys Ser Gln Tyr Val Val Phe Asn Ser Glu
    370                 375                 380

Gly Pro Lys Leu Gly Phe Ala Ala Gln Ala
385                 390

<210> SEQ ID NO 3
<211> LENGTH: 394
<212> TYPE: PRT
<213> ORGANISM: Aspergillus niger

<400> SEQUENCE: 3

Met Val Val Phe Ser Lys Thr Ala Ala Leu Val Leu Gly Leu Ser Ser
1               5                   10                  15

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Ile Asn Leu Pro Gly
        35                  40                  45

Met Tyr Ala Arg Ser Leu Ala Lys Phe Gly Gly Thr Val Pro Gln Ser
    50                  55                  60

Val Lys Glu Ala Ala Ser Lys Gly Ser Ala Val Thr Thr Pro Gln Asn
65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Val Phe Ser Asp
            100                 105                 110

Glu Leu Pro Ser Ser Glu Gln Thr Gly His Asp Leu Tyr Thr Pro Ser
        115                 120                 125

Ser Ser Ala Thr Lys Leu Ser Gly Tyr Thr Trp Asp Ile Ser Tyr Gly
    130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ala Ser Lys Ile
                165                 170                 175

Ser Ser Glu Phe Val Gln Asp Thr Ala Asn Asp Gly Leu Leu Gly Leu
            180                 185                 190

Ala Phe Ser Ser Ile Asn Thr Val Gln Pro Lys Ala Gln Thr Thr Phe
        195                 200                 205
```

```
Phe Asp Thr Val Lys Ser Gln Leu Asp Ser Pro Leu Phe Ala Val Gln
    210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
                245                 250                 255

Gly Tyr Trp Gly Phe Ser Thr Asp Gly Tyr Ser Ile Gly Asp Gly Ser
                260                 265                 270

Ser Ser Ser Ser Gly Phe Ser Ala Ile Ala Asp Thr Gly Thr Thr Leu
            275                 280                 285

Ile Leu Leu Asp Asp Glu Ile Val Ser Ala Tyr Tyr Glu Gln Val Ser
290                 295                 300

Gly Ala Gln Glu Ser Glu Glu Ala Gly Gly Tyr Val Phe Ser Cys Ser
305                 310                 315                 320

Thr Asn Pro Pro Asp Phe Thr Val Val Ile Gly Asp Tyr Lys Ala Val
                325                 330                 335

Val Pro Gly Arg Tyr Ile Asn Tyr Ala Pro Ile Ser Thr Gly Ser Ser
                340                 345                 350

Thr Cys Phe Gly Gly Ile Gln Ser Asn Ser Gly Leu Gly Leu Ser Ile
                355                 360                 365

Leu Gly Asp Val Phe Leu Lys Ser Gln Tyr Val Val Phe Asn Ser Glu
370                 375                 380

Gly Pro Lys Leu Gly Phe Ala Ala Gln Ala
385                 390

<210> SEQ ID NO 4
<211> LENGTH: 394
<212> TYPE: PRT
<213> ORGANISM: Aspergillus niger

<400> SEQUENCE: 4

Met Val Val Phe Ser Lys Thr Ala Ala Leu Val Leu Gly Leu Ser Ser
1               5                   10                  15

Ala Val Ser Ala Ala Pro Ala Pro Thr Arg Lys Gly Phe Thr Ile Asn
                20                  25                  30

Gln Ile Ala Arg Pro Ala Asn Lys Thr Arg Thr Ile Asn Leu Pro Gly
            35                  40                  45

Met Tyr Ala Arg Ser Leu Ala Lys Phe Gly Gly Thr Val Pro Gln Ser
50                  55                  60

Val Lys Glu Ala Ala Ser Lys Gly Ser Ala Val Thr Thr Pro Gln Asn
65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Val Phe Ser Asp
                100                 105                 110

Glu Leu Pro Ser Ser Glu Gln Thr Gly His Asp Leu Tyr Thr Pro Ser
            115                 120                 125

Ser Ser Ala Thr Lys Leu Ser Gly Tyr Thr Trp Asp Ile Ser Tyr Gly
        130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ala Ser Lys Ile
                165                 170                 175

Ser Ser Glu Phe Val Gln Asn Thr Ala Asn Asp Gly Leu Leu Gly Leu
                180                 185                 190
```

-continued

```
Ala Phe Ser Ser Ile Asn Thr Val Gln Pro Lys Ala Gln Thr Thr Phe
            195                 200                 205

Phe Asp Thr Val Lys Ser Gln Leu Asp Ser Pro Leu Phe Ala Val Gln
210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
            245                 250                 255

Gly Tyr Trp Gly Phe Ser Thr Asp Gly Tyr Ser Ile Gly Asp Gly Ser
                260                 265                 270

Ser Ser Ser Ser Gly Phe Ser Ala Ile Ala Asp Thr Gly Thr Thr Leu
            275                 280                 285

Ile Leu Leu Asp Asp Glu Ile Val Ser Ala Tyr Tyr Glu Gln Val Ser
290                 295                 300

Gly Ala Gln Glu Ser Glu Glu Ala Gly Gly Tyr Val Phe Ser Cys Ser
305                 310                 315                 320

Thr Asn Pro Pro Asp Phe Thr Val Val Ile Gly Asp Tyr Lys Ala Val
                325                 330                 335

Val Pro Gly Lys Tyr Ile Asn Tyr Ala Pro Ile Ser Thr Gly Ser Ser
            340                 345                 350

Thr Cys Phe Gly Gly Ile Gln Ser Asn Ser Gly Leu Gly Leu Ser Ile
                355                 360                 365

Leu Gly Asp Val Phe Leu Lys Ser Gln Tyr Val Val Phe Asn Ser Glu
            370                 375                 380

Gly Pro Lys Leu Gly Phe Ala Ala Gln Ala
385                 390

<210> SEQ ID NO 5
<211> LENGTH: 320
<212> TYPE: PRT
<213> ORGANISM: Aspergillus awamori
<220> FEATURE:
<221> NAME/KEY: misc_feature
<222> LOCATION: (257)..(257)
<223> OTHER INFORMATION: Xaa can be any naturally occurring amino acid

<400> SEQUENCE: 5

Ser Lys Gly Ser Ala Val Thr Thr Pro Gln Asn Asn Asp Glu Glu Tyr
1               5                   10                  15

Leu Thr Pro Val Thr Val Gly Lys Ser Thr Leu His Leu Asp Phe Asp
            20                  25                  30

Thr Gly Ser Ala Asp Leu Trp Val Phe Ser Asp Glu Leu Pro Ser Ser
                35                  40                  45

Glu Arg Thr Gly His Asn Val Tyr Thr Pro Ser Ser Ser Ala Thr Lys
            50                  55                  60

Leu Ser Gly Tyr Thr Trp Asn Ile Ser Tyr Gly Asn Gly Ser Ser Ala
65                  70                  75                  80

Ser Gly Asp Val Tyr Arg Asp Thr Val Thr Val Gly Gly Val Thr Asn
                85                  90                  95

Thr Lys Glu Ala Val Gln Ala Ala Ser Lys Ile Ser Ser Glu Phe Glx
            100                 105                 110

Glx Val Asx Gly Gly Glx Asx Ser Gly Ala Glx Ala Tyr Ser Ser Ile
        115                 120                 125

Asn Thr Val Gln Pro Lys Ala Gln Thr Thr Phe Phe Asp Thr Val Lys
        130                 135                 140
```

```
Ser Gln Leu Asn Ser Pro Leu Phe Ala Val Gln Leu Lys His Asp Ala
145                 150                 155                 160

Pro Gly Val Tyr Asp Phe Gly Tyr Ile Asx Asx Ser Lys Tyr Thr Gly
                165                 170                 175

Ser Ile Thr Tyr Thr Asp Ala Asp Ser Ser Glu Gly Tyr Trp Gly Phe
                180                 185                 190

Asn Pro Asn Gly Tyr Ser Ile Gly Asp Ser Ser Ser Gly Phe Ser
                195                 200                 205

Ala Ile Ala Asp Thr Gly Thr Thr Leu Ile Leu Leu Asp Asp Glu Ile
                210                 215                 220

Val Leu Asn Gly Ser Glx Val Ser Gly Gln Ala Asn Gln Glu Ala Asp
225                 230                 235                 240

Gly Gly Tyr Val Phe Asx Cys Ser Thr Thr Pro Pro Asp Phe Thr Gly
                245                 250                 255

Xaa Ile Gly Asp Tyr Lys Ala Val Gly Pro Lys Tyr Ile Asn Tyr Ala
                260                 265                 270

Pro Ser Asx Thr Pro Ser Thr Cys Phe Gly Gly Ile Gln Ser Asn Ser
                275                 280                 285

Gly Leu Gly Leu Ser Ile Leu Gly Asp Val Phe Leu Lys Ser Gln Tyr
290                 295                 300

Val Val Phe Asp Ser Gln Gly Pro Lys Leu Gly Phe Ala Ala Gln Ala
305                 310                 315                 320

<210> SEQ ID NO 6
<211> LENGTH: 395
<212> TYPE: PRT
<213> ORGANISM: Aspergillus fumigatus

<400> SEQUENCE: 6

Met Val Val Phe Ser Lys Val Thr Ala Val Val Gly Leu Ser Thr
1               5                   10                  15

Ile Val Ser Ala Val Pro Val Val Gln Pro Arg Lys Gly Phe Thr Ile
                20                  25                  30

Asn Gln Val Ala Arg Pro Val Thr Asn Lys Lys Thr Val Asn Leu Pro
                35                  40                  45

Ala Val Tyr Ala Asn Ala Leu Thr Lys Tyr Gly Gly Thr Val Pro Asp
    50                  55                  60

Ser Val Lys Ala Ala Ala Ser Ser Gly Ser Ala Val Thr Thr Pro Glu
65                  70                  75                  80

Gln Tyr Asp Ser Glu Tyr Leu Thr Pro Val Lys Val Gly Gly Thr Thr
                85                  90                  95

Leu Asn Leu Asp Phe Asp Thr Gly Ser Ala Asp Leu Trp Val Phe Ser
                100                 105                 110

Ser Glu Leu Ser Ala Ser Gln Ser Gly His Ala Ile Tyr Lys Pro
                115                 120                 125

Ser Ala Asn Ala Gln Lys Leu Asn Gly Tyr Thr Trp Lys Ile Gln Tyr
    130                 135                 140

Gly Asp Gly Ser Ser Ala Ser Gly Asp Val Tyr Lys Asp Thr Val Thr
145                 150                 155                 160

Val Gly Gly Val Thr Ala Gln Ser Gln Ala Val Glu Ala Ala Ser His
                165                 170                 175

Ile Ser Ser Gln Phe Val Gln Asp Lys Asp Asn Asp Gly Leu Leu Gly
                180                 185                 190

Leu Ala Phe Ser Ser Ile Asn Thr Val Ser Pro Arg Pro Gln Thr Thr
                195                 200                 205
```

```
Phe Phe Asp Thr Val Lys Ser Gln Leu Asp Ser Pro Leu Phe Ala Val
    210                 215                 220

Thr Leu Lys Tyr His Ala Pro Gly Thr Tyr Asp Phe Gly Tyr Ile Asp
225                 230                 235                 240

Asn Ser Lys Phe Gln Gly Glu Leu Thr Tyr Thr Asp Val Asp Ser Ser
                245                 250                 255

Gln Gly Phe Trp Met Phe Thr Ala Asp Gly Tyr Gly Val Gly Asn Gly
            260                 265                 270

Ala Pro Asn Ser Asn Ser Ile Ser Gly Ile Ala Asp Thr Gly Thr Thr
        275                 280                 285

Leu Leu Leu Leu Asp Asp Ser Val Val Ala Asp Tyr Tyr Arg Gln Val
    290                 295                 300

Ser Gly Ala Lys Asn Ser Asn Gln Tyr Gly Gly Tyr Val Phe Pro Cys
305                 310                 315                 320

Ser Thr Lys Leu Pro Ser Phe Thr Thr Val Ile Gly Gly Tyr Asn Ala
                325                 330                 335

Val Val Pro Gly Glu Tyr Ile Asn Tyr Ala Pro Val Thr Asp Gly Ser
            340                 345                 350

Ser Thr Cys Tyr Gly Gly Ile Gln Ser Asn Ser Gly Leu Gly Phe Ser
        355                 360                 365

Ile Phe Gly Asp Ile Phe Leu Lys Ser Gln Tyr Val Val Phe Asp Ser
    370                 375                 380

Gln Gly Pro Arg Leu Gly Phe Ala Pro Gln Ala
385                 390                 395

<210> SEQ ID NO 7
<211> LENGTH: 390
<212> TYPE: PRT
<213> ORGANISM: Aspergillus oryzae

<400> SEQUENCE: 7

Met Val Asn Thr Ser Leu Leu Ala Ala Leu Thr Ala Tyr Ala Val Ala
1               5                   10                  15

Val Ser Ala Ala Pro Thr Ala Pro Gln Val Lys Gly Phe Ser Val Asn
            20                  25                  30

Gln Val Ala Val Pro Lys Gly Val Tyr Arg His Pro Ala Ala Gln Leu
        35                  40                  45

Ala Lys Ala Tyr Gly Lys Tyr His Ala Thr Val Pro Thr Gln Val Ala
    50                  55                  60

Ala Ala Ala Ala Ala Thr Gly Ser Val Thr Thr Asn Pro Thr Ser Asn
65                  70                  75                  80

Asp Glu Glu Tyr Ile Thr Gln Val Thr Val Gly Asp Asp Thr Leu Gly
                85                  90                  95

Leu Asp Phe Asp Thr Gly Ser Ala Asp Leu Trp Val Phe Ser Ser Gln
            100                 105                 110

Thr Pro Ser Ser Glu Arg Ser Gly His Asp Tyr Tyr Thr Pro Gly Ser
        115                 120                 125

Ser Ala Gln Lys Ile Asp Gly Ala Thr Trp Ser Ile Ser Tyr Gly Asp
    130                 135                 140

Gly Ser Ser Ala Ser Gly Asp Val Tyr Lys Asp Lys Val Thr Val Gly
145                 150                 155                 160

Gly Val Ser Tyr Asp Ser Gln Ala Val Glu Ser Ala Glu Lys Val Ser
                165                 170                 175

Ser Glu Phe Thr Gln Asp Thr Ala Asn Asp Gly Leu Leu Gly Leu Ala
```

```
            180                 185                 190
Phe Ser Ser Ile Asn Thr Val Gln Pro Thr Pro Gln Lys Thr Phe Phe
            195                 200                 205

Asp Asn Val Lys Ser Ser Leu Ser Glu Pro Ile Phe Ala Val Ala Leu
210                 215                 220

Lys His Asn Ala Pro Gly Val Tyr Asp Phe Gly Tyr Thr Asp Ser Ser
225                 230                 235                 240

Lys Tyr Thr Gly Ser Ile Thr Tyr Thr Asp Val Asp Asn Ser Gln Gly
            245                 250                 255

Phe Trp Gly Phe Thr Ala Asp Gly Tyr Ser Ile Gly Ser Asp Ser Ser
            260                 265                 270

Ser Asp Ser Ile Thr Gly Ile Ala Asp Thr Gly Thr Thr Leu Leu Leu
            275                 280                 285

Leu Asp Asp Ser Ile Val Asp Ala Tyr Tyr Glu Gln Val Asn Gly Ala
            290                 295                 300

Ser Tyr Asp Ser Ser Gln Gly Gly Tyr Val Phe Pro Ser Ser Ala Ser
305                 310                 315                 320

Leu Pro Asp Phe Ser Val Thr Ile Gly Asp Tyr Thr Ala Thr Val Pro
            325                 330                 335

Gly Glu Tyr Ile Ser Phe Ala Asp Val Gly Asn Gly Gln Thr Phe Gly
            340                 345                 350

Gly Ile Gln Ser Asn Ser Gly Ile Gly Phe Ser Ile Phe Gly Asp Val
            355                 360                 365

Phe Leu Lys Ser Gln Tyr Val Val Phe Asp Ala Ser Gly Pro Arg Leu
370                 375                 380

Gly Phe Ala Ala Gln Ala
385                 390

<210> SEQ ID NO 8
<211> LENGTH: 394
<212> TYPE: PRT
<213> ORGANISM: Penicillium janthinellum

<400> SEQUENCE: 8

Met Val Val Phe Ser Lys Ile Thr Val Val Leu Ala Gly Leu Ala Thr
1               5                   10                  15

Val Ala Ser Ala Val Pro Thr Gly Thr Ser Arg Lys Ser Thr Phe Thr
            20                  25                  30

Val Asn Gln Lys Ala Arg Pro Val Ala Gln Ala Lys Ala Ile Asn Leu
        35                  40                  45

Pro Gly Met Tyr Ala Ser Ala Leu Ser Lys Tyr Gly Ala Ala Val Pro
50                  55                  60

Ala Ser Val Lys Ala Ala Ala Glu Ser Gly Thr Ala Val Thr Thr Pro
65                  70                  75                  80

Glu Ala Asn Asp Val Glu Tyr Leu Thr Pro Val Asn Val Gly Gly Thr
                85                  90                  95

Thr Leu Asn Leu Asp Phe Asp Thr Gly Ser Ala Asp Leu Trp Val Phe
            100                 105                 110

Ser Ser Glu Leu Ser Ser Ser Glu Ser Thr Gly His Ser Leu Tyr Lys
        115                 120                 125

Pro Ser Ser Asn Ala Thr Lys Leu Ala Gly Tyr Ser Trp Ser Ile Thr
    130                 135                 140

Tyr Gly Asp Gln Ser Ser Ala Ser Gly Asp Val Tyr Lys Asp Phe Val
145                 150                 155                 160
```

-continued

Val Val Gly Gly Val Lys Ala Ser Pro Gln Ala Val Glu Ala Ala Ser
                165                 170                 175

Gln Ile Ser Gln Gln Phe Val Asn Asp Lys Asn Asn Asp Gly Leu Leu
            180                 185                 190

Gly Leu Ala Phe Ser Ser Ile Asn Thr Val Lys Pro Lys Ser Gln Thr
            195                 200                 205

Thr Phe Phe Asp Thr Val Lys Gly Gln Leu Asp Ser Pro Leu Phe Ala
        210                 215                 220

Val Thr Leu Lys His Asn Ala Pro Gly Thr Tyr Asp Phe Gly Phe Val
225                 230                 235                 240

Asp Lys Asn Lys Tyr Thr Gly Ser Leu Thr Tyr Ala Gln Val Asp Ser
                245                 250                 255

Ser Gln Gly Phe Trp Ser Phe Thr Ala Asp Gly Tyr Lys Ile Gly Ser
            260                 265                 270

Lys Ser Gly Gly Ser Ile Gln Gly Ile Ala Asp Thr Gly Thr Thr Leu
            275                 280                 285

Leu Leu Leu Pro Asp Asn Val Val Ser Asp Tyr Tyr Gln Val Ser
        290                 295                 300

Gly Ala Gln Gln Asp Ser Ser Ala Gly Tyr Thr Val Pro Cys Ser
305                 310                 315                 320

Ala Gln Leu Pro Asp Phe Thr Val Thr Ile Gly Ser Tyr Asn Ala Val
                325                 330                 335

Val Pro Gly Ser Leu Ile Asn Tyr Ala Pro Leu Gln Ser Gly Ser Ser
            340                 345                 350

Thr Cys Phe Gly Ile Gln Ser Asn Ser Gly Leu Gly Phe Ser Ile
            355                 360                 365

Phe Gly Asp Ile Phe Leu Lys Ser Gln Tyr Val Val Phe Asp Ala Asn
370                 375                 380

Gly Pro Arg Leu Gly Phe Ala Pro Gln Ala
385                 390

<210> SEQ ID NO 9
<211> LENGTH: 395
<212> TYPE: PRT
<213> ORGANISM: Monascus purpureus

<400> SEQUENCE: 9

Met Val Val Phe Ser Lys Ile Thr Ala Val Ala Gly Phe Ser Thr
1               5                   10                  15

Leu Ala Ala Ala Met Pro Thr Leu Asn Arg Pro Asn Val Lys Ser Phe
            20                  25                  30

Ser Leu Ser Gln Ser Ala Ile Pro Arg Gln Gln Lys Asn Phe Asn Phe
        35                  40                  45

Ala Ala Thr Tyr Ala Lys Thr Leu Ala Lys Tyr Gly Gly Gln Ile Pro
    50                  55                  60

Ala Ser Leu Lys Ala Ala Ala Glu Lys Gly Ser Val Asn Thr Tyr Pro
65                  70                  75                  80

Glu Pro Gln Asp Ala Glu Tyr Leu Thr Ala Val Asp Val Gly Thr
                85                  90                  95

Thr Leu Asn Leu Asp Phe Asp Thr Gly Ser Ala Asp Leu Trp Val Phe
            100                 105                 110

Ser Ala Glu Leu Pro Ser Ser Glu Gln Ser Gly His Ala Ile Tyr Lys
        115                 120                 125

Pro Ser Gly Asn Ala Thr Lys Met Ser Gly Tyr Ser Trp Ser Ile Ser
    130                 135                 140

```
Tyr Gly Asp Gly Ser Ser Ala Ser Gly Asp Val Tyr Lys Asp Thr Val
145                 150                 155                 160

Thr Val Ala Gly Ile Thr Ala Pro Arg Gln Ala Val Glu Ala Ala Ser
            165                 170                 175

Thr Ile Ser Ser Glu Phe Thr Gln Asp Lys Asn Asn Asp Gly Leu Leu
        180                 185                 190

Gly Leu Ala Phe Ser Ser Ile Asn Thr Val His Pro Lys Ala Gln Thr
    195                 200                 205

Thr Trp Phe Asp Thr Val Lys Glu Asp Leu Asp Ser Pro Leu Phe Ala
210                 215                 220

Val Ala Leu Lys His Asn Ala Pro Gly Thr Phe Asp Phe Gly Tyr Val
225                 230                 235                 240

Asp Lys Ser Lys Tyr Thr Gly Ser Leu Thr Tyr Ala Asp Val Asp Asn
                245                 250                 255

Ser Gln Gly Phe Trp Gln Phe Thr Ala Asp Ser Tyr Ser Val Gly Ser
            260                 265                 270

Gln Ser Gly Ser Lys Ser Ile Val Gly Ile Ala Asp Thr Gly Thr Thr
        275                 280                 285

Leu Leu Leu Pro Asp Asp Val Val Glu Ala Tyr Tyr Lys Gln Val
    290                 295                 300

Glu Gly Ala Glu Asn Asp Ser Gln Ala Gly Gly Tyr Val Phe Pro Cys
305                 310                 315                 320

Asp Ser Gln Leu Pro Ser Phe Thr Ala Val Ile Asn Gly Tyr Ser Ala
                325                 330                 335

Val Val Pro Gly Ser Leu Ile Asn Tyr Ala Ser Ala Gly Asp Gly Ser
            340                 345                 350

Asn Asn Cys Leu Gly Gly Ile Gln Ser Asp Gln Gly Ile Gly Gln Ala
        355                 360                 365

Ile Phe Gly Asp Ile Phe Leu Lys Ser Gln Tyr Val Val Phe Asp Ala
370                 375                 380

Asp Gly Pro Arg Leu Gly Phe Ala Pro Gln Ala
385                 390                 395

<210> SEQ ID NO 10
<211> LENGTH: 397
<212> TYPE: PRT
<213> ORGANISM: Penicillium roqueforti

<400> SEQUENCE: 10

Met Val Val Phe Ser Gln Val Thr Val Ala Leu Thr Cys Phe Ser Ala
1               5                   10                  15

Ile Ala Ser Ala Ala Ala Val Arg Gln Glu Pro Pro Gln Gly Phe Thr
            20                  25                  30

Val Asn Gln Val Gln Lys Ala Val Pro Gly Thr Arg Thr Val Asn Leu
        35                  40                  45

Pro Gly Leu Tyr Ala Asn Ala Leu Val Lys Tyr Gly Ala Thr Val Pro
    50                  55                  60

Ala Thr Val His Ala Ala Val Ser Gly Ser Ala Ile Thr Thr Pro
65                  70                  75                  80

Glu Ala Asp Asp Val Glu Tyr Leu Thr Pro Val Thr Ile Gly Ser Ser
                85                  90                  95

Thr Leu Asn Leu Asp Phe Asp Thr Gly Ser Ala Asp Leu Trp Val Phe
            100                 105                 110

Ser Ser Glu Leu Thr Ser Ser Gln Gln Ser Gly His Asp Val Tyr Asn
```

```
            115                 120                 125
Val Gly Ser Leu Gly Thr Lys Leu Ser Gly Ala Ser Trp Ser Ile Ser
130                 135                 140

Tyr Gly Asp Gly Ser Ser Ala Ser Gly Asp Val Tyr Lys Asp Thr Val
145                 150                 155                 160

Thr Val Gly Gly Val Lys Ala Thr Gly Gln Ala Val Glu Ala Ala Lys
                165                 170                 175

Lys Ile Ser Ser Gln Phe Leu Gln Asp Lys Asn Asn Asp Gly Leu Leu
                180                 185                 190

Gly Met Ala Phe Ser Ser Ile Asn Thr Val Ser Pro Thr Pro Gln Lys
                195                 200                 205

Thr Phe Phe Asp Thr Val Lys Ser Ser Leu Gly Glu Pro Leu Phe Ala
210                 215                 220

Val Thr Leu Gln Gly Thr Gly Arg Pro Trp His Leu Arg Phe Gly Tyr
225                 230                 235                 240

Ile Asp Ser Asp Lys Tyr Thr Gly Thr Leu Ala Tyr Ala Asp Val Asp
                245                 250                 255

Asp Ser Asp Gly Phe Trp Ser Phe Thr Ala Asp Ser Tyr Lys Ile Gly
                260                 265                 270

Thr Gly Ala Ala Gly Lys Ser Ile Thr Gly Ile Ala Asp Thr Gly Thr
                275                 280                 285

Thr Leu Leu Leu Leu Asp Ser Ser Ile Val Thr Gly Leu Leu Gln Glu
                290                 295                 300

Gly Tyr Pro Gly Ser Gln Asn Ser Ser Ser Ala Gly Gly Tyr Ile Phe
305                 310                 315                 320

Pro Cys Ser Ala Thr Leu Pro Asp Phe Thr Val Thr Ile Asn Gly Tyr
                325                 330                 335

Asp Ala Val Val Pro Gly Lys Tyr Ile Asn Phe Ala Pro Val Ser Thr
                340                 345                 350

Gly Ser Ser Ser Cys Tyr Gly Gly Ile Gln Ser Asn Ser Gly Ile Gly
                355                 360                 365

Phe Ser Ile Phe Gly Asp Ile Phe Leu Lys Ser Gln Tyr Val Val Phe
370                 375                 380

Asp Ser Glu Gly Pro Arg Leu Gly Phe Ala Ala Gln Ala
385                 390                 395

<210> SEQ ID NO 11
<211> LENGTH: 406
<212> TYPE: PRT
<213> ORGANISM: Phaeosphaeria nodorum

<400> SEQUENCE: 11

Met Pro Ser Phe Thr Tyr Leu Thr Ala Ala Leu Ala Leu Thr Ser Ser
1               5                   10                  15

Val Val Ala Ser Pro Val Glu Lys Arg Asp Ala Phe Glu Val Lys Gln
                20                  25                  30

Val Ala His Gly Leu His Arg Lys Asn Gly Pro Ala Gln Ile Ala Lys
            35                  40                  45

Thr Leu Arg Lys Tyr Gly Lys Ala Val Pro Ala His Ile Gln Ala Ala
        50                  55                  60

Ala Asp Asn Asn Ala Val Val Gln Ala Asp Ala Asn Thr Gly Ser Asp
65                  70                  75                  80

Pro Ala Val Pro Ser Asp Gln Tyr Asp Ser Ser Tyr Leu Ser Pro Val
                85                  90                  95
```

-continued

Thr Val Gly Thr Ser Thr Val His Leu Asp Phe Asp Thr Gly Ser Ala
            100                 105                 110

Asp Leu Trp Val Phe Ser Asp Leu Gln Ala Lys Ser Ser Leu Ser Gly
        115                 120                 125

His Asp Tyr Tyr Lys Thr Asp Ala Ser Lys Arg Lys Ser Gly Tyr Thr
    130                 135                 140

Trp Lys Ile Ser Tyr Gly Asp Gly Ser Gly Ala Ser Gly Gln Val Tyr
145                 150                 155                 160

Thr Asp Lys Val Thr Val Gly Gln Val Thr Ala Thr Ala Gln Ala Val
                165                 170                 175

Glu Ala Ala Thr Ser Val Ser Ala Gln Phe Ser Gln Asp Val Asp Thr
            180                 185                 190

Asp Gly Leu Leu Gly Leu Ala Met Ser Ser Ile Asn Thr Val Lys Pro
        195                 200                 205

Gln Gln Gln Thr Thr Trp Phe Asp Thr Val Lys Ser Gln Leu Ala Lys
    210                 215                 220

Pro Leu Phe Ala Val Thr Leu Lys Tyr His Ala Ala Gly Thr Tyr Asp
225                 230                 235                 240

Phe Gly Tyr Ile Asp Ser Ala Lys Tyr Thr Gly Ala Ile Thr Tyr Val
                245                 250                 255

Asn Ala Asp Ala Ser Gln Gly Phe Trp Gly Phe Thr Ala Ser Gly Tyr
            260                 265                 270

Ser Val Gly Thr Gly Ala Thr Val Ser Ser Ile Ser Gly Ile Leu
        275                 280                 285

Asp Thr Gly Thr Thr Leu Met Tyr Val Pro Ala Ala Thr Ala Lys Ala
    290                 295                 300

Tyr Tyr Ala Lys Val Ser Gly Ala Lys Leu Asp Ser Thr Gln Gly Gly
305                 310                 315                 320

Tyr Val Phe Pro Cys Ser Ala Thr Leu Pro Asn Phe Ser Ile Thr Val
                325                 330                 335

Ala Gly Val Lys Gln Thr Val Pro Gly Lys Tyr Ile Asn Tyr Ala Pro
            340                 345                 350

Ile Thr Asp Gly Ser Ser Thr Cys Phe Gly Gly Met Gln Pro Asp Thr
        355                 360                 365

Asp Ile Gly Gln Ser Ile Phe Gly Asp Ile Phe Leu Lys Ser Lys Tyr
    370                 375                 380

Ile Val His Asp Met Ser Asn Gly Thr Pro Arg Leu Gly Phe Ala Gln
385                 390                 395                 400

Gln Ala Gly Val Ser Ser
                405

<210> SEQ ID NO 12
<211> LENGTH: 405
<212> TYPE: PRT
<213> ORGANISM: Trichoderma asperellum

<400> SEQUENCE: 12

Met Gln Thr Phe Gly Ala Phe Leu Val Ser Phe Leu Ala Ala Ser Gly
1               5                   10                  15

Met Ala Ala Ala Leu Pro Ala Glu Gly Gln Gln Lys Thr Ile Ser Val
            20                  25                  30

Pro Val Ile Tyr Asn Ala Asn His Ala Pro His Gly Pro Ser Ala Leu
        35                  40                  45

Tyr Lys Ala Lys Lys Lys Phe Gly Ala Pro Ile Ser Glu Ser Leu Lys
    50                  55                  60

-continued

```
Asn Asn Val Ala Gln His Lys Ala Ala Lys Leu Ala Arg Arg Gln Thr
 65              70              75              80

Gly Ser Ala Pro Asn His Pro Ser Asp Ser Glu Asp Glu Tyr Ile
             85              90              95

Thr Asn Val Ser Ile Gly Thr Pro Ala Gln Val Leu Pro Leu Asp Phe
            100             105             110

Asp Thr Gly Ser Ser Asp Leu Trp Val Phe Ser Ser Glu Thr Pro Ser
            115             120             125

Ser Gln Ala Lys Gly His Thr Leu Tyr Asn Pro Thr Lys Ser Ser Thr
130             135             140

Ser Lys Lys Leu Ser Gly Tyr Ser Trp Thr Ile Ser Tyr Gly Asp Gly
145             150             155             160

Ser Ser Ser Ser Gly Asp Val Tyr Thr Asp Thr Val Ser Val Gly Gly
                165             170             175

Phe Ser Val Thr Gly Gln Ala Val Glu Ser Ala Thr Lys Val Ser Ser
            180             185             190

Glu Phe Val Ser Asp Thr Ser Asn Ser Gly Leu Leu Gly Leu Ala Leu
            195             200             205

Asp Ser Ile Asn Thr Val Ser Pro Lys Gln Gln Lys Thr Trp Phe Ser
210             215             220

Asn Ala Ser Ser Lys Leu Ala Gln Pro Val Phe Thr Ala Asp Leu Asn
225             230             235             240

His Gln Ala Ser Gly Ser Tyr Asn Phe Gly Tyr Ile Asp Thr Ser Leu
            245             250             255

Ala Ser Gly Pro Ile Ser Tyr Val Pro Ile Ser Thr Ala Asn Gly Phe
            260             265             270

Trp Glu Phe Thr Ser Ala Ser Tyr Ala Ile Gly Ser Gly Ser Thr Lys
            275             280             285

Lys His Ser Thr Asp Gly Ile Ala Asp Thr Gly Thr Thr Leu Leu Leu
290             295             300

Leu Asp Asp Thr Ile Val Asp Ala His Tyr Gly Gln Val Ser Ser Ala
305             310             315             320

Gln Tyr Asp Asn Ser Gln Glu Gly Tyr Thr Phe Asp Cys Asp Glu Asn
            325             330             335

Leu Pro Ser Phe Thr Phe Ala Val Gly Ser Ser Lys Ile Thr Val Pro
            340             345             350

Gly Ser Leu Ile Asn Phe Ala Pro Val Ser Gly Asn Thr Cys Phe Gly
            355             360             365

Gly Leu Gln Ser Asn Asp Gly Ile Gly Ile Asn Ile Phe Gly Asp Val
            370             375             380

Ala Ile Lys Ala Ala Leu Val Val Phe Asp Leu Gly Asn Lys Arg Leu
385             390             395             400

Gly Trp Ala Gln Lys
            405
```

INCREASED FIBER HYDROLYSIS BY PROTEASE ADDITION

CROSS-REFERENCE TO RELATED APPLICATION

This application claims the benefit of U.S. Patent Application Ser. No. 60/998,818 filed Oct. 12, 2007. U.S. Patent Application Ser. No. 60/998,818 is incorporated by reference as if fully rewritten herein.

SEQUENCE LISTING

Following the Abstract of the Disclosure is set forth a paper copy of the SEQUENCE LISTING having SEQ ID NO:1 through SEQ ID NO:12. The SEQUENCE LISTING is incorporated by reference into this application.

BACKGROUND OF THE INVENTION

The following includes information that may be useful in understanding the present teachings. It is not an admission that any of the information provided herein is prior art, or material, to the presently described or claimed subject matter, or that any publication or document that is specifically or implicitly referenced is prior art.

FIELD OF THE INVENTION

The present teachings relate to, but are not limited to, the field of agricultural product production. Embodiments relate, for example, to methods for increasing the free glucose and other organic matter available from a fiber feedstock for fermentation and other applications.

BACKGROUND OF THE ART

A large quantity and variety of fiber feedstocks are available from agricultural processing operations. These fiber feedstocks (also called cellulosic feedstocks, biomass, or lignocellulosics) may be used, for example, to produce fuel, to produce industrial chemicals, or as other value-added food and feed products. A cellulosic feedstock is largely comprised of plant cell walls with cellulose, hemicellulose, lignin, and protein polymers as the primary constituents. The hydrolysis or breakdown of these feedstocks uses singly or a combination of enzymatic and thermochemical methods that result in the production of monomers and oligomers of carbohydrates. The hydrolyzed mix can serve as feedstocks to produce fuel, chemicals, and other products. Similar hydrolysis schemes are employed with most plant fibers that facilitate the release of glucose and other carbohydrates from fiber feedstocks.

Although attention has been paid to increasing the amount of glucose available from compositions such as uncooked granular starch (see, for example, U.S. Patent Application Publication No. 2006/0154354 A1, to Duan, et al.), lately more attention has been paid to methods for increasing the amount of usable carbohydrates obtained from readily available and inexpensive fiber feedstocks that contain no starch or minimal amounts of starch.

BRIEF SUMMARY OF THE INVENTION

Embodiments of the invention are typically directed to providing a method for increasing the amount of glucose and other carbohydrates obtained from hydrolysis of a low-starch or no-starch fiber stream by hydrolyzing the fiber stream in the presence of protease and one or more of cellulase and hemicellulase.

Embodiments include a method for increasing the amount of glucose and other organic matter released from a fiber feedstock, comprising reacting a fiber feedstock with a mixture of reactants comprising at least one protease and at least one member of the group consisting of cellulase and hemicellulase; and obtaining a reaction product from the fiber feedstock and the mixture of reactants comprising glucose. The amount of glucose in the reaction product (measured as a percentage of the fiber feedstock mass) is greater than the amount of glucose obtained from reaction of the fiber feedstock under the same conditions as the reaction including protease, but with at least one member selected from the group consisting of cellulase and hemicellulase and excluding protease. In some embodiments, the mixture of reactants used to increase the amount of glucose and other organic matter released from the fiber stream does not include amylases.

Proteases are enzymes that have found a great number of uses in the industrial production of detergents, animal hide processing, meat tenderizing as well as in other food applications involving animal and plant materials. As a group they represent one of the largest classes of hydrolytic enzymes which posses a wide range of specificities towards amino acid sequences, different pH and temperature optima, and different amino acids at active sites with some (i.e. metallo-proteases) requiring cations such as zinc or iron for optimal activity. Although a variety of proteases may be suitable for use in embodiments of the invention, typically an acid fungal protease is preferred. In one embodiment, the acid fungal protease has an amino acid sequence at least 95% identical to the amino acid sequence of SEQ ID NO: 1. In a further embodiment, the protease is selected from the group consisting of *Aspergillus saitoi* aspartic protease, or aspartic proteases from molds that are members of the genera of the *Ascomycetous* fungi represented by the genera *Aspergillus, Mucor, Rhizopus,* and *Penicillium*. In a typical embodiment, the protease is *Aspergillus saitoi* aspartic protease, which has the amino acid sequence of SEQ ID NO: 1.

A variety of fiber feedstocks are suitable for use in embodiments of the invention. Fiber feedstocks include, but are not limited to, corn stover, corn gluten feed (CGF), distillers' dried grains (DDG), distillers' dried grains with solubles (DDGS), switchgrass, miscanthus, soyhulls, wheat chaff, and wheat straw. In a typical embodiment, the fiber feedstock includes less than 20% starch by weight, less than 10% starch by weight, less than 5% starch by weight, or less than 1% starch by weight. In another embodiment, the fiber feedstock includes no starch.

A number of cellulases are suitable for use in typical embodiments of the invention. These include, for example, but are not limited to CELLUCLAST® (a Novozyme product), which is a 1,4-(1,3:1,4)-β-D-Glucan 4-glucano-hydrolase produced by submerged fermentation of the fungus *Trichoderma reesei*, deposited as ATCC No. 26921; or GC-220 (a Genencor product). Other useful cellulases include those from *T. reesei*, other species of *Trichoderma*, species of *Aspergillus*, species of *Crysosporium*, species of clostridium or cellulases from other bacterial and fungal species.

A variety of hemicellulases are suitable for use in typical embodiments of the invention, including, for example, but not limited to ULTRAFLO L (Novozyme), MULTIFECT XYLANASE (Genencor), VISCOZYME L (Novozyme), and VISCOSTAR L (Dyadic). The reaction products may also include one or more of arabinose, xylose, galactose, mannose, cellobiose, xylobiose, acetyl groups, phytosterols, phenolic compounds and oligomers of these compounds.

The amount of glucose in the reaction product (measured as a percentage of the fiber feedstock mass) following protease addition is greater than the amount of glucose obtained from reaction of the fiber feedstock without protease by at least 10%, at least 20%, at least 30%, at least 40%, at least 50%, at least 60%, at least 70%, at least 80%, at least 90%, or at least 100%.

A further embodiment includes a method for obtaining a solid residue from the enzyme treated fiber for the production of biooil, comprising preparing a glucose-enriched fiber feedstock reaction product as described in other embodiments of the invention, and separating said reaction product into a solid hydrolyzed fiber fraction and a liquid fraction. This solid fraction may then be used as a fuel for biooil production. The process employed in the above treatment is often referred to as hydrotreating, or HT. It can be used with fiber streams that contain a fairly high level of moisture typically greater than 50% on a wt/wt basis.

DETAILED DESCRIPTION OF THE INVENTION

The present teaching describes several different features and aspects of the invention with reference to various exemplary embodiments. It is understood, however, that the invention embraces numerous alternative embodiments, which may be accomplished by combining any of the different features and aspects described herein in any combination that one of ordinary skill in the art would find useful.

Processing methods as described herein may offer many advantages over the prior art. Of course, the scope of the invention is defined by the claims, and whether an embodiment is within that scope should not be limited by whether the method provides one or more of these advantages.

Current methods of processing corn, soy, wheat, barley, milo, canola, sunflower and other agricultural products to obtain useful commodities such as ethanol, animal feed, meals, and flours may also result in the production of a number of fiber byproducts. Processing methods include but are not limited to wet milling, dry milling, and modified wet milling. See Singh, et al. "Modified Dry Grind Ethanol Process," Ag. Eng. Dept., U. of Ill., UILU No. 2001-7021 (Jul. 18, 2001).

These byproducts, also referred to as fiber feedstocks, may include, for example, but are not limited to, corn stover, corn gluten feed, distillers' dried grains (DDG), distillers' dried grains with solubles (DDGS), switchgrass, soyhulls, wheat chaff, and wheat straw, palm fiber, bermuda grass, miscanthus and babassu. Fiber feedstocks do not necessarily need to be byproducts of any particular process to obtain some benefit from treatment according to embodiments presented herein. Fiber feedstocks may be pretreated chemically, thermally, and/or mechanically. More detail on fiber feedstocks, particularly corn fiber feedstocks, is found in U.S. Patent Application Publication No. 20060216396A1, to Abbas, et al., entitled "Corn Fiber Hulls as a Food Additive or Animal Feed," which is incorporated by reference herein.

Fiber feedstocks often benefit from further processing to produce more useful commodities, such as more readily digestible feed products, biofuel precursors, or industrial chemicals. Because typical byproducts are largely comprised of plant cell walls made of cellulose, hemicellulose, lignin, and proteins, their treatment typically includes enzymatic and/or thermochemical hydrolysis, which generates carbohydrate monomers and oligomers.

In some embodiments, the hydrolysis does not include any amylases. Amylases are glycoside hydrolase enzymes that break down starch into glucose molecules. Amylase is usually not necessary because the feedstocks have little or no starch. Alkaline treatment of the fiber feedstock while useful in extracting lignin and to break down ester linkages is not always necessary in a typical embodiment.

We have found that treatment of fiber feedstocks with protease prior to or in conjunction with enzymatic and/or thermochemical hydrolysis increases the amount of carbohydrate monomers and oligomers that may be obtained from the fiber feedstock, thereby increasing the commercial value of the fiber feedstock. Typically, the fiber feedstocks will either contain no starch prior to the protease treatment, or they will have only a small amount of starch. For example, the starch content of the fiber feedstock, by weight, may be less than 10%, less than 5%, less than 4%, less than 3%, less than 2%, less than 1%, or less than 0.5%.

A typical process of the invention includes thermochemical hydrolysis of a fiber feedstock. This releases some pentoses from the fiber hemicellulose constituent and loosens the fiber structures, particularly that of any remaining cell wall components. Following thermochemical hydrolysis, the fiber feedstock is treated enzymatically to release glucose and other hexoses, as well as to release pentoses including D-xylose and L-arabinose. A typical enzymatic treatment is conducted using a blend of enzymes including one or more cellulases and one or more hemicellulases, though one skilled in the art will recognize that this blend may be modified depending on the initial content of the fiber feedstock and on the results of the thermochemical hydrolysis.

In addition to including cellulases and hemicellulases, an enzymatic treatment includes one or more proteases. Although applicants do not wish to be bound by theory, it is believed that the proteases degrade primarily the structural proteins that are cross-liked to other components of the fiber feedstock. In many cases the carbohydrate polymers are linked predominantly via N or O type linkages to the amino acids: asparagine, glutamine, serine, hydroxyproline or threonine that are present in the polypeptide backbone. This increases the amount of glucose and other hexoses that are released during the enzymatic treatment. This also reduces the amount of cellulase necessary in a typical hydrolysis.

As used herein, "cellulase" or "cellulase blend" include one enzyme or a mixture of enzymes that degrade cellulose. Typical cellulases include endocellulase or endoglucanase, exocellulase, exocello-biohydrolase, and cellobiase. "Hemicellulase" or "hemicellulase blend" include one enzyme or a mixture of enzymes that hydrolyze hemicellulose. Typical hemicellulases include but are not limited to β-xylanases, α-arabinofuranosidases, ferulic and acetyl esterases, α & β-mannases, α & β-galactosidases, and β-galactomannanases.

The effective amount of cellulase, hemicellulase, and protease used in embodiments of the invention will vary with the type of enzymes used in the process, the ultrastructure and composition of the cell wall (which varies by plant type), the pretreatment or pre-processing step, and well as the as the desired yield. Commercial enzymes may be used according to their manufacturer's instructions.

Typical proteases for use in the invention include, for example, the aspartic protease from *Aspergillus saitoi* having the amino acid sequence give in SEQ ID NO:1. Other proteases having at least 50% or greater sequence identity with SEQ ID NO:1 may also be used, so long as the protease activity is conserved. Proteases suitable for use in embodiments of the invention may have a sequence identity with SEQ ID NO: 1 of greater than 50%, greater than 60%, greater than 70%, greater than 80%, greater than 90%, greater than 95%, or greater than 98%, so long as protease activity is retained.

For example, other suitable proteases include but are not limited to those given in Table 1. The *Aspergillus saitoi* protease protein sequence was used to blast the NCBI sequence collection and identify proteases with 47% or higher sequence identity. The *T. reesei* protease was not identified because of too many gaps between the two protease sequences. Sequence identity percentages are based on percentage identity with SEQ ID NO:1. Sequence identity percentages were determined by BLAST in the CGC Wisconsin Genetics Software Packages, Version 10 (available from Accelrys Inc., 9685 Scranton Road, San Diego, Calif., USA). Alignments using BLAST programs can be performed using the default parameters.

TABLE 1

Sequence Identity comparison of protease from *Aspergillus saitoi* with proteases from other organisms.

| Source | Sequence identity % | E value | Sequence ID |
|---|---|---|---|
| aspergillopepsin A precursor [*Aspergillus niger*] | 99% | 2e−180 | SEQ ID NO: 2 |
| preproproctase B [*Aspergillus niger*] | 97% | 3e−147 | SEQ ID NO: 3 |
| aspartic proteinase aspergillopepsin I pepA-*Aspergillus niger* | 97% | 5e−141 | SEQ ID NO: 4 |
| Aspergillopepsin A precursor | 96% | 9e−140 | SEQ ID NO: 5 |
| aspartic endopeptidase Pep1/aspergillopepsin F [*Aspergillus fumigatus* Af293] | 71% | 1e−134 | SEQ ID NO: 6 |
| *Aspergillus Oryzae* Aspartic Proteinase | 71% | 4e−103 | SEQ ID NO: 7 |
| propenicillopepsin-JT2 precursor [*Penicillium janthinellum*] | 67% | 1e−109 | SEQ ID NO: 8 |
| acid proteinase [*Monascus purpureus*] | 63% | 4e−124 | SEQ ID NO: 9 |
| aspartic proteinase [*Penicillium roquefortii*] | 64% | 5e−119 | SEQ ID NO: 10 |
| aspartic protease [*Phaeosphaeria nodorum*] | 53% | 1e−94 | SEQ ID NO: 11 |
| aspartyl protease [*Trichoderma asperellum*] | 47% | 5e−60 | SEQ ID NO: 12 |

Reaction conditions for hydrolysis including protease need not vary from those typically used for hydrolysis using cellulases or hemicellulases without proteases. For example, reaction temperatures may be, for example, but are not limited to between 25 to 80° C., 40 to 70° C. or 50 to 60° C. Reaction times may be, for example, but are not limited to between 30 minutes to 48 hours, typically between 60 minutes and 24 hours. Reaction pH may be, for example, from 2.0 to 7.0, more typically from 4.0 to 5.5. Based on results obtained earlier and present knowledge of acid proteases, some of the reactions may proceed at lower pH (<5.0) and at higher temperature (>55 C). With different fiber materials, the optimum enzyme performance may occur over a wide range of temperature and pH.

EXAMPLES

The examples below are only representative of some aspects of the invention. These examples should not be interpreted as limiting the invention in any way not explicitly stated in the claims.

Example 1

Example 1 shows hydrolysis of various fiber feedstocks with and without a protease. Percentages are calculated on a V/V basis. A mixture of 250 mg fiber feedstock in 5 ml of 100 mM citrate buffer at pH 5.0, an enzyme solution of 0.2% cellulase mix (including 0.2% GC-220, a Genencor cellulase blend; 0.2% CELLUCLAST L, a Novozymes cellulase blend, and 0.1% Novozyme 28074), 0.2% hemicellulase mix (ULTRAFLO L, a Novozymes hemicellulase blend), and an aspartic protease from *Aspergillus saitoi* having SEQ ID NO: 1 were placed in a shaker at 55.degree. C. for about 48 hours. Fiber feedstocks were prepared by grinding with a Wiley mill and sieving through a 40 mesh screen. Fiber feedstocks used in the experiment were corn fiber, corn stover, corn gluten feed, distillers' dried grains, distillers' dried grains with solubles, switchgrass, soyhulls, wheat chaff, and wheat straw.

A control experiment was also conducted for each of the fiber feedstocks. The control did not include the protease, but otherwise the conditions and amounts were the same.

Samples of each reaction were spun, and the supernatant was used for glucose analysis. Glucose concentration was obtained using an analyzer from YSI, Incorporated. Results are shown in Table 2. The amount of available glucose was increased over the control by up to 130%. The corn fiber showed a negligible improvement, with only a 0.5% increase. This negligible increase is believed to be due to the presence of a relatively high amount of starch in the corn fiber.

TABLE 2

Percent of glucose released from different feedstocks by cellulase and hemicellulases with and without the protease
Glucose Released (% of total dry weight)

| Fiber Streams | No Protease | Protease | % Improvement |
|---|---|---|---|
| Corn Fiber | 19.8 | 19.9 | 0.5 |
| Corn Stover | 15.2 | 17.4 | 14.5 |
| Corn Gluten Feed | 6.0 | 13.8 | 130.0 |
| DDG | 14 | 20.4 | 45.7 |
| DDGS | 6.8 | 12.2 | 79.4 |
| Switchgrass | 11 | 14 | 27.3 |
| Soyhulls | 22.0 | 32.4 | 47.3 |
| Wheat Chaff | 10.8 | 13.8 | 27.7 |
| Wheat Straw | 12.6 | 17 | 34.9 |

Patents, patent applications, publications, scientific articles, books, web sites, and other documents and materials referenced or mentioned herein are indicative of the levels of skill of those skilled in the art to which the inventions pertain, as of the date each publication was written, and all are incorporated by reference as if fully rewritten herein. Inclusion of a document in this specification is not an admission that the document represents prior invention or is prior art for any purpose.

The terms and expressions employed herein have been used as terms of description and not of limitation, and there is no intention in the use of such terms and expressions, or any portions thereof, to exclude any equivalents now known or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples.

It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:

1. A method for increasing the amount of glucose and other sugar and peptides released from a fiber containing corn or soy bean byproduct comprising:

(a) reacting a fiber containing corn or soy bean byproduct selected from the group consisting of corn gluten feed (CGF), distillers dried grains (DDG), distillers dried grains with solubles (DDGS), and soy hulls with a mixture of reactants comprising at least one protease and at least one member of the group consisting of cellulase and hemicellulase; and (b) obtaining a reaction product from said fiber containing corn or soy byproduct and said mixture of reactants, wherein a wt/wt ratio of glucose/fiber is greater in the reaction product than the wt/wt ratio of glucose/fiber obtained from reaction of the fiber containing corn or soy processing byproduct under the same conditions as the reaction of step (a), but excluding protease, and (c) forming an animal feed from the reaction product.

2. The method of claim 1, wherein said mixture does not include amylase.

3. The method of claim 1, wherein said protease is an acid fungal protease.

4. The method of claim 1, wherein said protease has an amino acid sequence at least 95% identical to the amino acid sequence of SEQ ID NO: 1.

5. The method of claim 1, wherein said protease is selected from the group consisting of *Aspergillus saitoi* aspartic protease, *Penicillium* acid protease, *Mucor* acid protease, *Monascus* acid protease, *Trichoderma* acid protease, *Phaeosphaeria* acid protease, and *Rhizopus* acid protease.

6. The method of claim 4, wherein said protease is *Aspergillus saitoi* aspartic protease, said *Aspergillus saitoi* aspartic protease having the amino acid sequence of SEQ ID NO: 1.

7. The method of claim 1, wherein said corn or soy bean byproduct is selected from the group consisting of CGF, DDG, and DDGS.

8. The method of claim 1, wherein said fiber feedstock comprises less than 20% starch by weight.

9. The method of claim 1, wherein said fiber feedstock comprises less than 10% starch by weight.

10. The method of claim 1, wherein said fiber feedstock comprises less than 5% starch by weight.

11. The method of claim 1, wherein said fiber feedstock comprises 0% starch by weight.

12. The method of claim 1, wherein said mixture of reactants comprises cellulase, and wherein said cellulase comprises one or more of endo-β-1,4 glucanases, exo-cellobiohydrolases, β-glucosidase, and exoglucanases.

13. The method of claim 1, wherein said mixture of reactants comprises hemicellulase, and wherein said hemicellulase comprises one or more of endo-1,4-β-xylanase, β-xylosidase, β-endomannanase, β-mannosidase, pectin lyase, pectate lyase, α-L-arabinofuransidase, α-glucuronidases, α/β-galactosidases, and several esterases.

14. The method of claim 1, wherein said reaction product further comprises arabinose, xylose, galactose, mannose, cellobiose, maltose, and maltotriose.

15. The method of claim 1, wherein the wt/wt ratio of glucose/fiber is greater in the reaction product than the wt/wt ratio of glucose/fiber amount of glucose obtained from reaction of the fiber containing corn or soy byproduct under the same conditions as the reaction of step (a), but excluding protease by at least 10%.

16. The method of claim 15, wherein the wt/wt ratio of glucose/fiber is greater in the reaction product than the wt/wt ratio of glucose/fiber amount of glucose obtained from reaction of the fiber containing corn or soy byproduct under the same conditions as the reaction of step (a), but excluding protease by at least 20%.

17. The method of claim 16, wherein the wt/wt ratio of glucose/fiber is greater in the reaction product than the wt/wt ratio of glucose/fiber amount of glucose obtained from reaction of the fiber containing corn or soy byproduct under the same conditions as the reaction of step (a), but excluding protease by at least 100%.

18. The method of claim 1, wherein said protease has an amino acid sequence selected from the group consisting of SEQ ID NO: 1, SEQ ID NO:2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

19. A method for obtaining a solid hydrolyzed fiber, comprising: (a) preparing a reaction product according to claim 1; and (b) separating said reaction product into a solid hydrolyzed fiber fraction and a liquid fraction, wherein at least one of the hydrolyzed fiber fraction the liquid fraction are used to form the animal feed.

* * * * *